United States Patent [19]

Sanchika et al.

[11] Patent Number: 5,767,284
[45] Date of Patent: Jun. 16, 1998

[54] PROCESS FOR PRODUCING A POLYOXYALKYLENE DERIVATIVE SUBSTITUTED WITH SUCCINIMIDYL GROUP

[75] Inventors: Kouzoh Sanchika; Tohru Yasukohchi; Kei-ichi Maruyama, all of Kawasaki; Syunsuke Ohhashi, Yokohama, all of Japan

[73] Assignee: NOF Corporation, Tokyo, Japan

[21] Appl. No.: 868,261

[22] Filed: Jun. 3, 1997

[30] Foreign Application Priority Data

Nov. 5, 1996 [JP] Japan ................................. 8-308785

[51] Int. Cl.$^6$ ................................................. C07D 207/12
[52] U.S. Cl. ...................................................... 548/520
[58] Field of Search ........................................... 548/520

[56] References Cited

U.S. PATENT DOCUMENTS 5,484,945  1/1996  Nagatomo et al. .................... 548/520

*Primary Examiner*—Patricia L. Morris
*Attorney, Agent, or Firm*—Young & Thompson

[57] ABSTRACT

A process for producing a polyoxyalkylene derivative substituted with succinimidyl group which comprises reacting a polyoxyalkylene compound having carboxyl group at ends with N-hydroxysuccinimide in an inert solvent in the presence of dicyclohexylcarbodiimide; filtering an obtained reaction product; and crystallizing the polyoxyalkylene derivative substituted with succinimidyl group by adding isopropyl alcohol to a filtrate obtained by the filtration, an amount by weight of isopropyl alcohol being 1 to 100 times as much as an amount by weight of the polyoxyalkylene compound having carboxyl group at ends.

Materials can be handled with safety in the process of the present invention, and a highly pure polyoxyalkylene derivative substituted with succinimidyl group which does not cause turbidity in an aqueous solution and has an excellent quality as a material for drugs can be produced.

4 Claims, No Drawings

PROCESS FOR PRODUCING A POLYOXYALKYLENE DERIVATIVE SUBSTITUTED WITH SUCCINIMIDYL GROUP

FIELD OF THE INVENTION

The present invention relates to a process for producing a polyoxyalkylene derivative substituted with succinimidyl group. More particularly, the present invention relates to a process for producing a highly pure polyoxyalkylene derivative substituted with succinimidyl group which is mainly used for drugs, for example, for modification of polypeptides, physiologically active proteins, and enzymes with polyoxyalkylene groups, and modification with polyoxyalkylene groups in drug delivery systems using liposomes and polymer micells.

PRIOR ART OF THE INVENTION

In recent years, many attempts have been made for stabilizing drugs by chemical modification of physiologically active proteins and enzymes. Among these attempts, chemical modification with a polyoxyalkylene derivative has long been made, and polyoxyalkylene derivatives having carboxyl group at the end of the molecule are known as typical examples of such a polyoxyalkylene derivative.

It is already disclosed that polyoxyalkylene compounds having carboxyl group at the end can generally be transformed into an activated polyoxyalkylene derivative substituted with succinimidyl group by the reaction with N-hydroxysuccinimide in the presence of dicyclohexylcarbodiimide to increase the reactivity with substances for the modification such as physiologically active proteins (the specifications of Japanese Patent Application Laid-Open No. Showa 62(1987)-185029, Japanese Patent Application Laid-Open No. Showa 63(1988)-60938, and Japanese Patent Application Laid-Open No. Heisei 4(1992)-164098).

Heretofore, for preparation of a polyoxyalkylene derivative substituted with succinimidyl group, a polyoxyalkylene compound having carboxyl group at the end is brought into reaction with N-hydroxysuccinimide in an inert solvent such as dimethylformamide in the presence of dicyclohexylcarbodiimide. After the reaction has been completed, formed dicyclohexylurea is removed by filtration, and the filtrate is added into ethyl ether or petroleum ether dropwise to precipitate the polyoxyalkylene derivative substituted with succinimidyl group as the product (for example, the specification of Japanese Patent Application Laid-Open No. Showa 62(1987)-89630, and A. Abuchowski et al., Cancer Biochem. Biophys. Volume 7, Pages 175 to 186, published in 1984).

In recent years, it is required that polyoxyalkylene derivatives used for chemical modification of physiologically active proteins or drug delivery systems using liposome be produced in a controlled environment such as a clean room. In the production of polyoxyalkylene derivatives substituted with succinimidyl group, using a large amount of an ether in the crystallization process is not preferable in view of handling because ethyl ether and petroleum ether which have heretofore been used are volatile, and the danger of causing fire is large. When the precipitation is conducted by using petroleum ether, complete removal of dicyclohexylurea formed from dicyclohexylcarbodiimide during the reaction is sometimes difficult. When dicyclohexylurea is left remaining in the polyoxyalkylene derivative substituted with succinimidyl group, an aqueous solution of the derivative becomes turbid, and using such a derivative as a raw material for drugs is not desirable.

SUMMARY OF THE INVENTION

Accordingly, the present invention has an object of providing a process for producing a highly pure polyoxyalkylene derivative substituted with succinimidyl group which enables handling of materials with safety and provides the polyoxyalkylene derivative not causing turbidity in an aqueous solution and having an excellent quality as a material for drugs.

As the result of the extensive studies conducted by the present inventors to solve the above problems, it was discovered that dicyclohexylurea can effectively be removed by reacting a polyoxyalkylene compound having carboxyl group at the end with N-hydroxysuccinimide in the presence of dicyclohexylcarbodiimide, filtering the obtained reaction mixture, and crystallizing the polyoxyalkylene derivative substituted with succinimidyl group by adding isopropyl alcohol to the filtrate obtained by the filtration. The present invention has been completed on the basis of the discovery.

Thus, the present invention provides:

(1) A process for producing a polyoxyalkylene derivative substituted with succinimidyl group which is represented by general formula [2]:

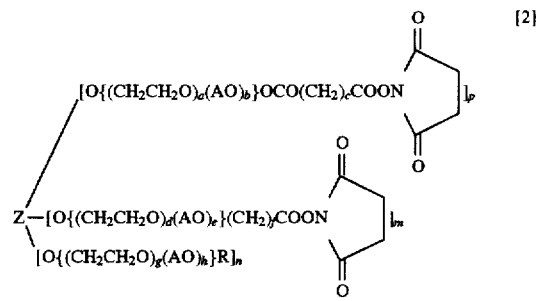

(wherein Z represents a residue group derived from a compound having 2 to 4 hydroxyl groups; R represents hydrogen atom or a hydrocarbon group having 1 to 24 carbon atoms; AO represents an oxyalkylene group having 3 or 4 carbon atoms; a, d and g represent each an average number by mol of addition of oxyethylene group which is 0 to 1,000, and a+d+g=30 to 1,000; b, e, and h represent each an average number by mol of addition of oxyalkylene group which is 0 to 200; (b+e+h)/(a+d+g)=0 to 0.2; the oxyethylene groups and the oxyalkylene groups are added to each other randomly or to form blocks; c represents 1 to 4; f represents 1 to 3; p represents 0 to 4; m represents 0 to 4; n represents 0 to 3; p and m do not simultaneously represent 0; and p+m+n=2 to 4) which comprises reacting a polyoxyalkylene compound having carboxyl group at ends which is represented by general formula [1]:

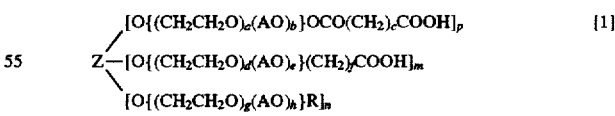

(wherein Z represents a residue group derived from a compound having 2 to 4 hydroxyl groups; R represents hydrogen atom or a hydrocarbon group having 1 to 24 carbon atoms; AO represents an oxyalkylene group having 3 or 4 carbon atoms; a, d and g represent each an average number by mol of addition of oxyethylene group which is 0 to 1,000, and a+d+g=30 to 1,000; b, e, and h represent each an average number by mol of addition of oxyalkylene group which is 0 to 200; (b+e+h)/(a+d+g)=0 to 0.2; the oxyethylene groups and the oxyalkylene groups are added to each other randomly or to form blocks; c represents 1 to 4; f represents 1 to 3; p represents 0 to 4; m represents 0 to 4; n represents 0 to 3; p and m do not simultaneously represent 0; and p+m+n=2 to 4) with N-hydroxysuccinimide in an inert solvent in the presence of dicyclohexylcarbodiimide; filtering an obtained reaction product; and crystallizing the compound represented by general formula [2] by adding isopropyl alcohol to a filtrate obtained by the filtration, an amount by weight of isopropyl alcohol being 1 to 100 times as much as an amount by weight of the compound represented by general formula [1];

(2) A process according to claim 1, wherein the crystallization of the compound represented by general formula [2] is repeated by repeating procedures of dissolving the compound represented by general formula [2] which has been separated by preceding crystallization in an inert solvent and crystallizing the compound represented by general formula [2] from an obtained solution by adding isopropyl alcohol;

(3) A process according to claim 1, wherein isopropyl alcohol is added at a temperature of 0° C. or lower in an amount by weight 2 to 50 times as much as an amount by weight of the compound represented by general formula [1]; and (4) A process according to claim 2, wherein isopropyl alcohol is added at a temperature of 0° C. or lower in an amount by weight 2 to 50 times as much as an amount by weight of the compound represented by general formula [1].

DETAILED DESCRIPTION OF THE INVENTION

In the present invention, a polyoxyalkylene compound having carboxyl group at the end which is represented by general formula [1]:

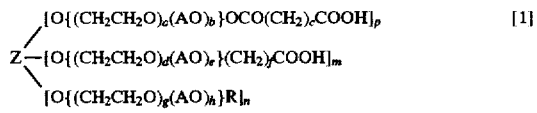

is used as the starting material. In general formula [1], Z represents a residue group derived from a compound having 2 to 4 hydroxyl groups; R represents hydrogen atom or a hydrocarbon group having 1 to 24 carbon atoms; AO represents an oxyalkylene group having 3 or 4 carbon atoms; a, d and g represent each the average number by mol of addition of oxyethylene group which is 0 to 1,000, and a+d+g=30 to 1,000; b, e, and h represent each the average number by mol of addition of oxyalkylene group which is 0 to 200; (b+e+h)/(a+d+g)=0 to 0.2; the oxyethylene groups and the oxyalkylene groups are added to each other randomly or to form blocks; c represents 1 to 4; f represents 1 to 3; p represents 0 to 4; m represents 0 to 4; n represents 0 to 3; p and m do not simultaneously represent 0; and p+m+n=2 to 4.

Examples of the compound having 2 to 4 hydroxyl groups which provides the residue group represented by Z in general formula [1] include ethylene glycol, propylene glycol, 1,2-butylene glycol, 1,3-butylene glycol, 2,3-butylene glycol, tetramethylene glycol, glycerol, diglycerol, erythritol, 1,3,5-pentanetriol, trimethylolethane, trimethylolpropane, and pentaerythritol.

Examples of the hydrocarbon group having 1 to 24 carbon atoms which is represented by R in general formula [1] include saturated or unsaturated linear or branched aliphatic hydrocarbon groups, such as methyl group, ethyl group, propyl group, isopropyl group, butyl group, isobutyl group, tertiary-butyl group, pentyl group, isopentyl group, hexyl group, isoheptyl group, 2-ethylhexyl group, octyl group, isononyl group, decyl group, dodecyl group, isotridecyl group, tetradecyl group, hexadecyl group, octadecyl group, isostearyl group, oleyl group, octyldodecyl group, docosyl group, and decyltetradecyl group; and aromatic hydrocarbon groups, such as benzyl group, cresyl group, butylphenyl group, dibutylphenyl group, octylphenyl group, nonylphenyl group, dodecylphenyl group, dioctylphenyl group, and dinonylphenyl group. Among these groups, methyl group, ethyl group, and propyl group are particularly preferable.

Examples of the oxyalkylene group having 3 or 4 carbon atoms which is represented by AO in general formula [1] include oxypropylene group, oxybutylene group, and oxytetramethylene group. These oxyalkylene groups can be formed by addition polymerization of propylene oxide, 1,2-butylene oxide, or tetrahydrofuran.

In general formula [1], a, d, and g represent each the average number of addition of oxyethylene group. a, d, and g represent each 0 to 1,000, and the total of a, d, and g is 30 to 1,000. When the total of a, d, and g is less than 30, there is the possibility that forming precipitates is difficult in the crystallization. When the total of a, d, and g is more than 1,000, there is the possibility that the viscosity is excessively high to cause inferior workability.

In general formula [1], b, e, and h represent each the average number of addition of an oxyalkylene group having 3 or 4 carbon atoms. b, e, and g represent each 0 to 200. The ratio (b+e+h)/(a+d+g) which is the ratio of the number of addition of the oxyalkylene group having 3 or 4 carbon atoms to the number of addition of oxyethylene group is 0 to 0.2. When the ratio of the number of addition of the oxyalkylene group having 3 or 4 carbon atoms to the number of addition of oxyethylene group is more than 0.2, the polyoxyalkylene derivative substituted with succinimidyl group tends to be liquid to cause difficulty in forming precipitates in the crystallization.

In general formula [1], c and f represent each the number of methylene group. c represents 1 to 4, and f represents 1 to 3. Either when c represents 5 or more or when f represents 4 or more, the raw material is difficult to obtain.

In general formula [1], p, m, and n represent each the number of the functional group at the end in the residue group represented by Z which is derived from the compound having hydroxyl groups. p represents 0 to 4, m represents 0 to 4, and n represents 0 to 3. p+m+n is 2 to 4. In general formula [1], p and m do not simultaneously represent 0, i.e., the compound represented by general formula [1] has at least one carboxyl group.

In the process of the present invention, the polyoxyalkylene compound having carboxyl group at the end which is represented by general formula [1] is brought into reaction with N-hydroxysuccinimide in an inert solvent in the presence of dicyclohexylcarbodiimide to synthesize the polyalkylene derivative substituted with succinimidyl group which is represented by general formula [2]:

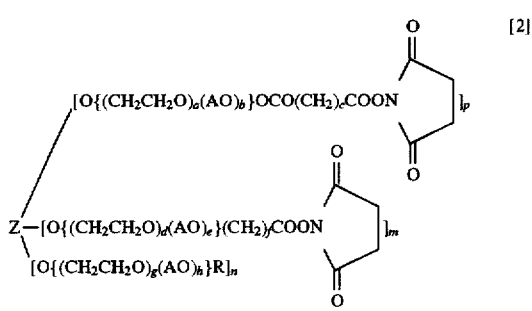

In general formula [2], Z represents a residue group derived from a compound having 2 to 4 hydroxyl groups; R represents hydrogen atom or a hydrocarbon group having 1 to 24 carbon atoms; AO represents an oxyalkylene group having 3 or 4 carbon atoms; a, d and g represent each the average number by mol of addition of oxyethylene group which is 0 to 1,000, and a+d+g=30 to 1,000; b, e, and h represent each the average number by mol of addition of oxyalkylene group which is 0 to 200; (b+e+h)/(a+d+g)=0 to 0.2; the oxyethylene groups and the oxyalkylene groups are added to each other randomly or to form blocks; c represents 1 to 4; f represents 1 to 3; p represents 0 to 4; m represents 0 to 4; n represents 0 to 3; p and m do not simultaneously represent 0; and p+m+n=2 to 4.

In the process of the present invention, any type of solvent can be used as the inert solvent in the reaction of the compound represented by general formula [1] with N-hydroxysuccinimide without any restriction as long as the solvent has neither hydroxyl group nor carboxyl group. Examples of such an inert solvent include chloroform, dichloromethane, 1,1-dichloroethane, acetone, tetrahydrofuran, acetonitrile, dimethyl-formamide, dimethylsulfoxide, benzene, and toluene. Among these solvents, dichloromethane, dimethylformamide, and toluene are particularly preferably used. A solvent having hydroxyl group such as methanol reacts with the carboxyl group at the end of the polyoxyalkylene compound in competition with N-hydroxysuccinimide. When a compound having carboxyl group such as acetic acid is used as the solvent, the solvent reacts with N-hydroxysuccinimide in competition with the carboxyl group at the end of the polyoxyalkylene compound. Therefore, such compounds are not preferable.

In the process of the present invention, the amount by mol of N-hydroxysuccinimide which is used for the reaction with the compound represented by general formula [1] is preferably 1.0 to 2.0 times, more preferably 1.2 to 1.7 times, as much as the amount by mol of the carboxyl group in the compound represented by general formula [1]. When the amount by mol of N-hydroxysuccinimide is less than the amount by mol of the carboxyl group in the compound represented by general formula [1], unreacted carboxyl group which is not substituted with N-succinimidyl group is left remaining. When the amount by mol of N-hydroxysuccinimide is more than 2.0 times as much as the amount by mol of the carboxyl group in the compound represented by general formula [1], the amount of N-hydroxysuccinimide which does not take part in the reaction is increased, and the process is economically disadvantageous. Moreover, the complete removal of the unreacted N-hydroxysuccinimide by the crystallization becomes difficult, and there is the possibility that the purity of the polyoxyalkylene derivative substituted with succinimidyl group is decreased.

In the process of the present invention, the amount by mol of dicyclohexylcarbodiimide which is present in the reaction of the compound represented by general formula [1] and N-hydroxy-succinimide is preferably 1.0 to 2.0 times, more preferably 1.2 to 1.7 times, as much as the amount by mol of the carboxyl group in the compound represented by general formula [1]. When the amount by mol of dicyclohexylcarbodiimide is less than the amount by mol of the carboxyl group in the compound represented by general formula [1], there is the possibility that the reaction does not proceed sufficiently. When the amount by mol of dicyclohexylcarbodiimide is more than 2.0 times as much as the amount by mol of the carboxyl group in the compound represented by general formula [1], the process is economically disadvantageous. Moreover, the complete removal of the excess amount of dicyclohexylcarbodiimide by the crystallization becomes difficult, and there is the possibility that the purity of the polyoxyalkylene derivative substituted with succinimidyl group is decreased.

In the process of the present invention, the temperature of the reaction of the compound represented by general formula [1] with N-hydroxysuccinimide is preferably 5° to 40° C., more preferably 15° to 35° C. When the temperature of the reaction is lower than 5° C., the reaction is slow. Therefore, a long time is required for the reaction, and there is the possibility that the conversion of the reaction is not increased sufficiently. When the temperature of the reaction is higher than 40° C., there is the possibility that undesirable side reactions, such as decomposition of succinimidyl group, take place. The time of the reaction of the compound represented by general formula [1] with N-hydroxysuccinimide is preferably 2 to 30 hours, more preferably 5 to 24 hours. When the time of the reaction is less than 2 hours, the reaction of the carboxyl group at the end of the compound represented by general formula [1] with N-hydroxysuccinimide does not sufficiently proceed, and there is the possibility that unreacted carboxyl group is left remaining. As the time of the reaction, 30 hours are generally sufficient. When the reaction is continued for more than 30 hours, there is the possibility that undesirable side reactions, such as decomposition of succinimidyl group, take place.

In the process of the present invention, the compound represented by general formula [1] is brought into reaction with N-hydroxysuccinimide in the presence of dicyclohexylcarbodiimide. Dicyclohexylurea formed by the reaction of dicyclohexylcarbodiimide with water is removed from the reaction solution by filtration, and the filtrate containing the polyoxyalkylene derivative substituted with succinimidyl group which is represented by general formula [2] is separated.

The material of the filter used for the filtration is not particularly limited as long as crystal of dicyclohexylurea which is hardly soluble in the solvent used for the reaction can be removed. In general, filters which retain particles having diameters of 1 to 10 μm, have resistance to the solvent, and are made of various materials, such as paper and glass, can be used. The method of the filtration is not particularly limited, and various methods, such as filtration under an added pressure or under a reduced pressure and centrifugal filtration, can be used.

In the process of the present invention, the compound represented by general formula [2] is crystallized by adding isopropyl alcohol to the filtrate which is obtained by removing dicyclohexylurea from the reaction mixture by the filtration. The amount by weight of the added isopropyl alcohol is 1 to 100 times, preferably 2 to 50 time, as much as the amount by weight of the compound represented by general formula [1]. When the amount by weight of isopropyl alcohol is less than the amount by weight of the compound represented by general formula [1], the compound represented by general formula [2] is not sufficiently crystallized, and there is the possibility that the compound represented by general formula [2] is left remaining in the solution. When the amount by weight of isopropyl alcohol is more than 100 times as much as the amount by weight of the compound represented by general formula [1], the total volume is increased to cause increase in the time for the filtration, and the workability is decreased. Moreover, there is the possibility that the yield of polyoxyalkylene derivative substituted with succinimidyl group is decreased.

Isopropyl alcohol used in the process of the present invention for the crystallization has the flash temperature of 120° C. which is higher than the flash temperatures of conventionally used ethyl ether (−45° C.) and petroleum ether (−18° C. or lower), and the danger of causing fire is smaller.

In the process of the present invention, isopropyl alcohol which is added to the filtrate containing the reaction product is preferably cooled to 50° C. or lower, more preferably 0° C. or lower. By cooling isopropyl alcohol, the yield of the compound represented by general formula [2] is increased. The addition of isopropyl alcohol to the filtrate is conducted slowly while the filtrate is stirred. After the compound represented by general formula [2] has been crystallized, the resultant mixture is stirred for 1 to 2 hours. Then, the compound represented by general formula [2] which has been crystallized can be separated by filtration under an increased pressure or under a reduced pressure or by centrifugal filtration. The separated compound represented by general formula [2] is preferably washed with an aliphatic hydrocarbon having 5 to 8 carbon atoms in an amount by weight 3 to 10 times as much as the amount by weight of the compound represented by general formula [1]. The compound represented by general formula [2] which has been separated and washed is preferably dried in vacuo at 20° to 35° C. for 10 to 25 hours.

In the process of the present invention, the crystallization of the compound represented by general formula [2] by addition of isopropyl alcohol may be conducted only once or repeatedly. For the repeated crystallization, the compound represented by general formula [2] which has been precipitated by crystallization is dissolved to prepare a solution, and the compound represented by general formula [2] is crystallized again from the obtained solution. The solvent used for preparing the solution by dissolving the compound represented by general formula [2] after the preceding crystallization is not particularly limited. The same solvent as that used for the reaction may be used, or a solvent different from that used for the reaction may be used. The purity of the polyoxyalkylene derivative substituted with succinimidyl group is increased by the repeated crystallization. Therefore, the number of repeating of the crystallization can suitably be selected in accordance with the required purity of the polyoxyalkylene derivative substituted with succinimidyl group.

To summarize the advantages of the present invention, materials can be handled with safety in the process of the present invention, and a highly pure polyoxyalkylene derivative substituted with succinimidyl group which does not cause turbidity in an aqueous solution because the content of residual dicyclohexylurea is small and has an excellent quality as a material for drugs can be produced.

EXAMPLES

The present invention is described in more detail with reference to examples in the following.

Example 1

In a four-necked flask, 200 g (22.7 mmol) of polyoxyethylene bis(carboxymethyl) ether represented by general formula [3]:

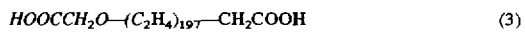

$$HOOCCH_2O-(C_2H_4)_{197}-CH_2COOH \quad (3)$$

was dissolved into 400 g of dichloromethane, and the temperature of the resultant solution was kept at 30° C. while the solution was stirred. To this solution, 7.8 g (68.2 mmol) of N-hydroxysuccinimide and 14.0 g (68.2 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 2,000 g of isopropyl alcohol which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 400 g of dichloromethane, and crystal was precipitated again from the resultant solution by adding dropwise 2,000 g of isopropyl alcohol which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 250° C. for 12 hours to obtain 174 g (the yield: 85.1%) of an activated polyoxyethylene derivative substituted with succinimidyl group which is expressed by formula [4]:

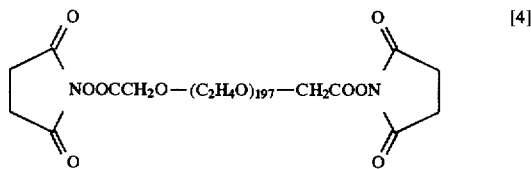

$$NOOCCH_2O-(C_2H_4O)_{197}-CH_2COON \quad [4]$$

The degree of activation of the carboxyl group at the end (the fraction of the carboxyl group converted into the imidoester) of the obtained polyoxyethylene derivative was 97.5% as obtained by the measurement of $^1$H-NMR. A 10% by weight aqueous solution of this polyoxyethylene derivative showed a transmittance of light of 650 nm of 96.4%.

Example 2

In a four-necked flask, 200 g (20.0 mmol) of polyoxyethylene monomethyl ether monosuccinate represented by general formula [5]:

$$CH_3O-(C_2H_4O)_{224}-COC_2H_4COOH \quad (5)$$

was dissolved into 400 g of dimethylformamide, and the temperature of the resultant solution was kept at 30° C. while the solution was stirred. To this solution, 3.5 g (30.0 mmol) of N-hydroxysuccinimide and 6.2 g (30.0 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 1,500 g of isopropyl alcohol which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 400 g of dimethylformamide, and crystal was precipitated again from the resultant solution by adding dropwise 1,500 g of isopropyl alcohol which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 25° C. for 12 hours to obtain 183 g (the yield: 90.6%) of an activated polyoxyethylene succinate substituted with succinimidyl group which is expressed by formula [6]:

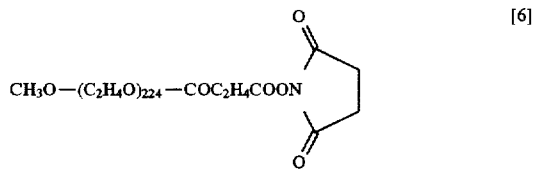

The degree of activation of the carboxyl group at the end of the obtained compound was 96.9% as obtained by the measurement of $^1$H-NMR. A 10% by weight aqueous solution of this polyoxyethylene derivative showed a transmittance of light of 650 nm of 97.1%.

Example 3

In a four-necked flask, 200 g (100.9 mmol) of polyoxyethylene monomethyl monocarboxymethyl ether represented by general formula [7]:

$$CH_3O-(C_2H_4O)_{43}-CH_2COOH \qquad (7)$$

was dissolved into 450 g of toluene, and the temperature of the resultant solution was kept at 30° C. while the solution was stirred. To this solution, 17.4 g (151.4 mmol) of N-hydroxysuccinimide and 31.2 g (151.4 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 2,000 g of isopropyl alcohol which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 450 g of toluene, and crystal was precipitated again from the resultant solution by adding dropwise 2,000 g of isopropyl alcohol which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 25° C. for 12 hours to obtain 169 g (the yield: 80.6%) of an activated polyoxyethylene derivative substituted with succinimidyl group which is expressed by formula [8]:

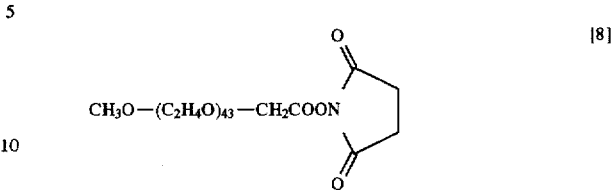

The degree of activation of the carboxyl group at the end of the obtained compound was 98.1% as obtained by the measurement of $^1$H-NMR. A 10% by weight aqueous solution of this polyoxyethylene derivative showed a transmittance of light of 650 nm of 96.9%.

Example 4

In a four-necked flask, 200 g (20.0 mmol) of polyoxyethylene-polyoxypropylene monomethyl ether monosuccinate represented by general formula [9]:

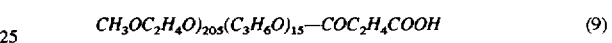

$$CH_3O(C_2H_4O)_{205}(C_3H_6O)_{15}-COC_2H_4COOH \qquad (9)$$

was dissolved into 400 g of dimethylformamide, and the temperature of the resultant solution was kept at 30° C. while the solution was stirred. To this solution, 3.4 g (29.9 mmol) of N-hydroxysuccinimide and 6.2 g (29.9 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 1,500 g of isopropyl alcohol which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 400 g of dimethylformamide, and crystal was precipitated again from the resultant solution by adding dropwise 1,500 g of isopropyl alcohol which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 25° C. for 12 hours to obtain 184 g (the yield: 91.1%) of an activated polyoxyethylene succinate substituted with succinimidyl group which is expressed by formula [10]:

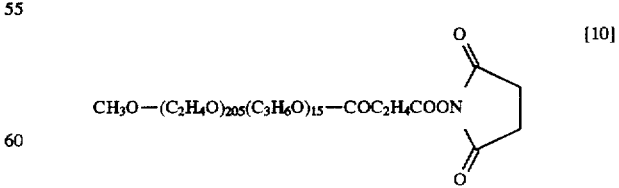

The degree of activation of the carboxyl group at the end of the obtained compound was 97.0% as obtained by the measurement of $^1$H-NMR. A 10% by weight aqueous solution of this polyoxyethylene derivative showed a transmittance of light of 650 nm of 98.0%.

Example 5

In a four-necked flask, 200 g (10.0 mmol) of glycerol polyoxyethylene tris(carboxymethyl ether) represented by general formula [11]:

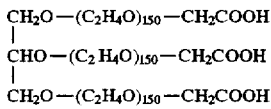

was dissolved into 400 g of dimethylformamide, and the temperature of the resultant solution was kept at 30° C. while the solution was stirred. To this solution, 5.2 g (44.9 mmol) of N-hydroxysuccinimide and 9.2 g (44.9 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 1,500 g of isopropyl alcohol which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 400 g of dimethylformamide, and crystal was precipitated again from the resultant solution by adding dropwise 1,500 g of isopropyl alcohol which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 25° C. for 12 hours to obtain 185 g (the yield: 91.2%) of an activated polyoxyethylene derivative substituted with succinimidyl group which is expressed by formula [12]:

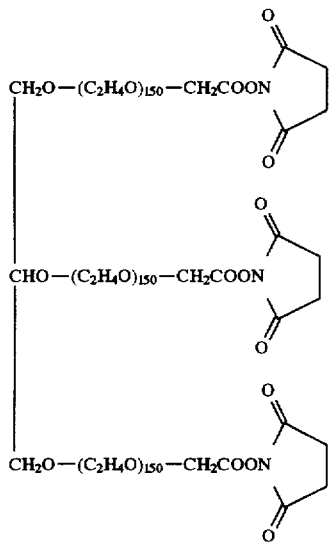

The degree of activation of the carboxyl group at the end of the obtained compound was 95.7% as obtained by the measurement of $^1$H-NMR. A 10% by weight aqueous solution of this polyoxyethylene derivative showed a transmittance of light of 650 nm of 97.7%.

Example 6

In a four-necked flask, 200 g (19.9 mmol) of glycerol polyoxyethylene tris(succinate) represented by general formula [13]:

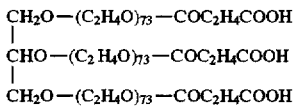

was dissolved into 400 g of dichloromethane, and the temperature of the resultant solution was kept at 30° C. while the solution was stirred. To this solution, 10.3 g (89.7 mmol) of N-hydroxysuccinimide and 18.5 g (89.7 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 2,000 g of isopropyl alcohol which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 400 g of dichloromethane, and crystal was precipitated again from the resultant solution by adding dropwise 2,000 g of isopropyl alcohol which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 25° C. for 12 hours to obtain 179 g (the yield: 87.0%) of an activated polyoxyethylene tris(succinate) substituted with succinimidyl group which is expressed by formula [14]:

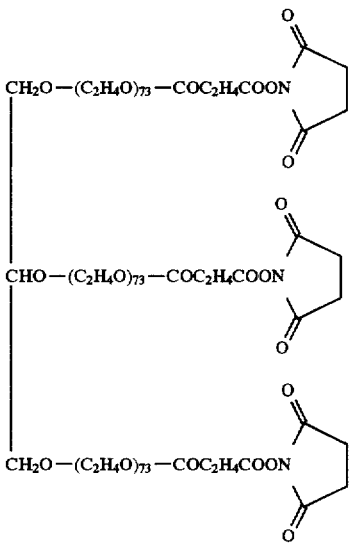

The degree of activation of the carboxyl group at the end of the obtained compound was 98.0% as obtained by the measurement of $^1$H-NMR. A 10% by weight aqueous solution of this polyoxyethylene derivative showed a transmittance of light of 650 nm of 97.5%.

Example 7

In a four-necked flask, 200 g (39.9 mmol) of polyoxyethylene monomethyl monocarboxymethyl ether represented by general formula [15]:

$$CH_3O-(C_2H_4O)_{112}-CH_2COOH \qquad (15)$$

was dissolved into 400 g of dichloromethane, and the temperature of the resultant solution was kept at 30° C. while the solution was stirred. To this solution, 6.9 g (59.8 mmol) of N-hydroxysuccinimide and 12.3 g (59.8 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 2,000 g of isopropyl alcohol which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 400 g of dichloromethane, and crystal was precipitated again from the resultant solution by adding dropwise 2,000 g of isopropanol which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 25° C. for 12 hours to obtain 165 g (the yield: 80.9%) of an activated polyoxyethylene derivative substituted with succinimidyl group which is expressed by formula [16]:

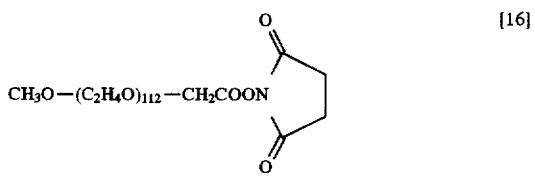

The degree of activation of the carboxyl group at the end of the obtained compound was 99.0% as obtained by the measurement of $^1$H-NMR. A 10% by weight aqueous solution of this polyoxyethylene derivative showed a transmittance of light of 650 nm of 98.8%.

Comparative Example 1

In a four-necked flask, 200 g (20.0 mmol) of polyoxyethylene monomethyl ether monosuccinate represented by general formula [5]:

$$CH_3O-(C_2H_4O)_{224}-COC_2H_4COOH \qquad (5)$$

was dissolved into 400 g of dimethylformamide, and the temperature of the resultant solution was kept at 30° C. while the solution was stirred. To this solution, 3.5 g (30.0 mmol) of N-hydroxysuccinimide and 6.2 g (30.0 mmol) of dicyclohexylcarbodiimide were added, and the reaction was allowed to proceed at 30° C. for 15 hours. The reaction solution became turbid as the reaction proceeded.

After the reaction was completed, the reaction solution was filtered under an increased pressure by using No.5A filter paper (the diameter of retained particles: 7 μm; a product of ADVANTEC Company) to remove dicyclohexylurea. To the filtrate, 1,500 g of ethyl ether which had been cooled to 0° C. was added dropwise to precipitate crystal. After the resultant mixture was stirred for 1 hour, the formed crystal was separated by the centrifugal filtration at 2,000 rpm for 15 minutes.

The obtained crystal was dissolved into 400 g of dimethylformamide, and crystal was precipitated again from the resultant solution by adding dropwise 1,500 g of ethyl ether which had been cooled to 0° C. After the resultant mixture was stirred for 1 hour, the formed crystal was separated by the centrifugal filtration at 2,000 rpm for 15 minutes. In the final step, the obtained crystal was washed with 1,000 g of hexane and separated by the centrifugal filtration at 2,000 rpm for 15 minutes.

The obtained crystal was dried in vacuo at 25° C. for 12 hours to obtain 180 g (the yield: 89.1%) of an activated polyoxyethylene succinate substituted with succinimidyl group which is expressed by formula [6]:

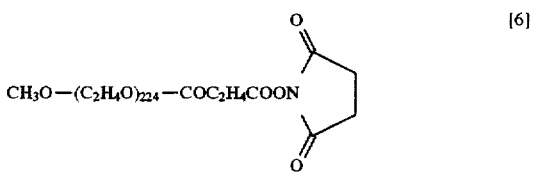

The degree of activation of the carboxyl group at the end of the obtained compound was 96.5% as obtained by the measurement of $^1$H-NMR. A 10% by weight aqueous solution of this polyoxyethylene derivative showed a transmittance of light of 650 nm of 80.5%.

The solvent used for the crystallization, the yield of the polyoxyalkylene derivative substituted with succinimidyl group, the degree of activation of the carboxyl group at the end, and the transmittance of light of 650 nm shown by the 10% by weight aqueous solution of the polyoxyethylene derivative in Examples 1 to 7 and Comparative Example 1 are summarized in Table 1.

TABLE 1

|  | non-solvent used in crystallization* | | degree of | |
| --- | --- | --- | --- | --- |
|  | isopropyl alcohol | ethyl ether | yield (%) | activation (%) | transmittance (%) |
| Example 1 | 10 | — | 85.1 | 97.5 | 96.4 |
| Example 2 | 7.5 | — | 90.6 | 96.9 | 97.1 |
| Example 3 | 10 | — | 80.6 | 98.1 | 96.9 |
| Example 4 | 7.5 | — | 91.1 | 97.0 | 98.0 |
| Example 5 | 7.5 | — | 91.2 | 95.7 | 97.7 |
| Example 6 | 10 | — | 87.0 | 98.0 | 97.5 |
| Example 7 | 10 | — | 80.9 | 99.0 | 98.8 |
| Comparative Example 1 | — | 7.5 | 89.1 | 96.5 | 80.5 |

*: The amount of the non-solvent used in the crystallization is shown in terms of the ratio by weight of the amount of the non-solvent to the amount of the polyoxyalkyene compound having carboxyl group at the end which was used as the raw material.

It can be understood from the results shown in Table 1 that the polyoxyalkylene derivatives substituted with succinimidyl group in Examples 1 to 7 which were produced in accordance with the process of the present invention had high degrees of activation of the carboxyl group at the end and contained only small amounts of impurities as exhibited by the high transmittances of a light of 650 nm shown by the 10% by weight aqueous solutions. In contrast, the polyoxyalkylene derivative substituted with succinimidyl group in Comparative Example 1 which was obtained by crystallization by adding ethyl ether contained impurities in a larger amount than those in the polyoxyalkylene derivatives substituted with succinimidyl group in Examples 1 to 7 as exhibited by the lower transmittance of light of 650 nm shown by 10% by weight aqueous solution of the polyoxyalkylene derivative obtained in Comparative Example 1.

What is claimed is:

1. A process for producing a polyoxyalkylene derivative substituted with succinimidyl group which is represented by general formula:

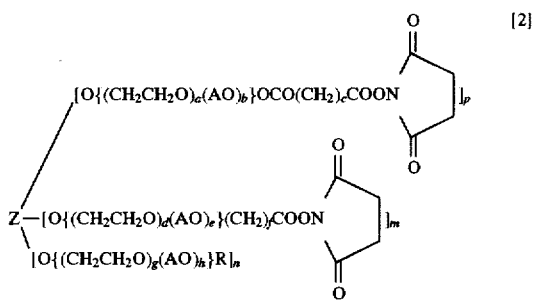

[2]

(wherein Z represents a residue group derived from a compound having 2 to 4 hydroxyl groups; R represents hydrogen atom or a hydrocarbon group having 1 to 24 carbon atoms; AO represents an oxyalkylene group having 3 or 4 carbon atoms; a, d and g represent each an average number by mol of addition of oxyethylene group which is 0 to 1,000, and a+d+g=30 to 1,000; b, e, and h represent each an average number by mol of addition of oxyalkylene group which is 0 to 200; (b+e+h)/(a+d+g)=0 to 0.2; the oxyethylene groups and the oxyalkylene groups are added to each other randomly or to form blocks; c represents 1 to 4; f represents 1 to 3; p represents 0 to 4; m represents 0 to 4; n represents 0 to 3; p and m do not simultaneously represent 0; and p+m+n=2 to 4) which comprises reacting a polyoxyalkylene compound having carboxyl group at ends which is represented by general formula:

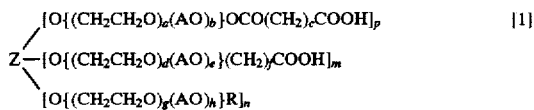

[1]

(wherein Z represents a residue group derived from a compound having 2 to 4 hydroxyl groups; R represents hydrogen atom or a hydrocarbon group having 1 to 24 carbon atoms; AO represents an oxyalkylene group having 3 or 4 carbon atoms; a, d and g represent each an average number by mol of addition of oxyethylene group which is 0 to 1,000, and a+d+g=30 to 1,000; b, e, and h represent each an average number by mol of addition of oxyalkylene group which is 0 to 200; (b+e+h)/(a+d+g)=0 to 0.2; the oxyethylene groups and the oxyalkylene groups are added to each other randomly or to form blocks; c represents 1 to 4; f represents 1 to 3; p represents 0 to 4; m represents 0 to 4; n represents 0 to 3; p and m do not simultaneously represent 0; and p+m+n=2 to 4) with N-hydroxysuccinimide in an inert solvent in the presence of dicyclohexylcarbodiimide; filtering an obtained reaction product; and crystallizing the compound represented by general formula by adding isopropyl alcohol to a filtrate obtained by the filtration, an amount by weight of isopropyl alcohol being 1 to 100 times as much as an amount by weight of the compound represented by general formula.

2. A process according to claim 1, wherein the crystallization of the compound represented by general formula is repeated by repeating procedures of dissolving the compound represented by general formula which has been separated by preceding crystallization in an inert solvent and crystallizing the compound represented by general formula from an obtained solution by adding isopropyl alcohol.

3. A process according to claim 1, wherein isopropyl alcohol is added at a temperature of 0° C. or lower in an amount by weight 2 to 50 times as much as an amount by weight of the compound represented by general formula.

4. A process according to claim 2, wherein isopropyl alcohol is added at a temperature of 0° C. or lower in an amount by weight 2 to 50 times as much as an amount by weight of the compound represented by general formula.

* * * * *